US012613323B2

(12) United States Patent
Erlöv

(10) Patent No.: US 12,613,323 B2
(45) Date of Patent: Apr. 28, 2026

(54) ULTRASOUND SYSTEM AND METHOD

(71) Applicant: MEDQUS Innovations AB, Höör (SE)

(72) Inventor: Tobias Erlöv, Höör (SE)

(73) Assignee: MEDQUS INNOVATIONS AB, Höör (SE)

( * ) Notice: Subject to any disclaimer, the term of this patent is extended or adjusted under 35 U.S.C. 154(b) by 97 days.

(21) Appl. No.: 18/574,898

(22) PCT Filed: Jun. 28, 2022

(86) PCT No.: PCT/EP2022/067698
§ 371 (c)(1),
(2) Date: Dec. 28, 2023

(87) PCT Pub. No.: WO2023/275030
PCT Pub. Date: Jan. 5, 2023

(65) Prior Publication Data
US 2024/0319350 A1     Sep. 26, 2024

(30) Foreign Application Priority Data

Jul. 2, 2021     (SE) .................................... 2150866-8

(51) Int. Cl.
G01S 7/52 (2006.01)
A61B 8/00 (2006.01)
(Continued)

(52) U.S. Cl.
CPC .......... G01S 7/52028 (2013.01); A61B 8/085 (2013.01); A61B 8/0891 (2013.01);
(Continued)

(58) Field of Classification Search
CPC ............. G01S 15/8915; G01S 7/52028; G01S 7/52036; A61B 8/085; A61B 8/0891;
(Continued)

(56) References Cited

U.S. PATENT DOCUMENTS

| | | | |
|---|---|---|---|
| 7,285,094 B2 | 10/2007 | Nohara et al. | |
| 2004/0039282 A1 | 2/2004 | Szabo et al. | |
| 2009/0043197 A1 | 2/2009 | Umemura et al. | |

FOREIGN PATENT DOCUMENTS

| | | |
|---|---|---|
| WO | 2009146414 A1 | 12/2009 |
| WO | 2020016449 A1 | 1/2020 |

OTHER PUBLICATIONS

Erlöv, Tobias, Determining carotid plaque vulnerability using ultrasound center frequency shifts; Atherosclerosis 2016 pp. 293-300.

(Continued)

*Primary Examiner* — Amelie R Davis
(74) *Attorney, Agent, or Firm* — DINSMORE & SHOHL LLP

(57)     ABSTRACT

An ultrasound system includes an ultrasound transducer configured to transmit a plurality of ultrasound signals from a plurality of elements in a transducer array to a region of interest. The ultrasound transducer is configured to receive and sample a plurality of backscattered ultrasound signals from the region of interest. A processing unit is configured to calculate a local phase parameter in the time-domain for each of the plurality of backscattered ultrasound signals and calculate a center frequency for each of the local phase parameters. A beamformer is configured to perform receiver beamforming by summing the center frequencies. The ultrasound system is further configured to generate at least one parameter representative of a physical property of the region of interest based on the summed center frequencies. An ultrasound method for generating at least one parameter representative of a physical property of a region of interest is also disclosed.

11 Claims, 6 Drawing Sheets

(51) Int. Cl.
A61B 8/08 (2006.01)
G01S 15/89 (2006.01)
(52) U.S. Cl.
CPC ........ A61B 8/4488 (2013.01); G01S 7/52036
(2013.01); G01S 15/8915 (2013.01)
(58) Field of Classification Search
CPC ... A61B 8/4488; A61B 8/5207; A61B 8/5223;
A61B 8/5269
See application file for complete search history.

(56) References Cited

OTHER PUBLICATIONS

Erlöv, Tobias, Scatterer size estimation using the center frequency assessed from ultrasound time domain data, pp. 2352-2357; J. Acoust. Soc. Am. 140 (4), Oct. 2016.
Gehlbach, S.M., Scatterer-Induced Frequency Variations in Reflected Acoustic Pulses: Implications for Tissue Characterization, Ultrasonic Imaging 7, 172-178 (1985).

301

ULTRASOUND SYSTEM AND METHOD

CROSS-REFERENCE TO RELATED APPLICATIONS

This application is the U.S. National Stage of PCT/EP2022/067698 filed on Jun. 28, 2022, which claims priority to Sweden Patent Application 2150866-8 filed on Jul. 2, 2021, the entire content of both are incorporated herein by reference in their entirety.

FIELD OF THE INVENTION

The present disclosure relates to an ultrasound system, in particular an ultrasound imaging system, and an ultrasound method, in particular an ultrasound imaging method. The disclosed ultrasound system and method involve improvements regarding the ability to calculate and/or extract parameters representative of physical properties of a region of interest, such as characterizing of the atherosclerotic plaque in an artery wall of a subject.

BACKGROUND OF THE INVENTION

Medical ultrasound is an imaging technique based on ultrasound. The technique may be used to create images of body structures. Its aim is often to find a source of a disease, but it is also used for other purposes such as examination of pregnant women. Ultrasound is sound waves with frequencies which are higher than those audible to humans. Ultrasonic images, also known as sonograms, are made by employing a transducer having elements arranged in a transducer array. The elements in the transducer array cause ultrasound waves to propagate into a medium. When the ultrasound waves are reflected by an object or other variations in the medium, the reflected ultrasound waves are received by the transducer. The received signals can then be processed to create an image.

In the processing of ultrasound waves, beamforming may be applied for both transmission and reception to improve the directivity as well as the sensitivity of resulting data. In general terms, beamforming can be referred to as a technique to control electronic parameterization and signal transformation for the generation of ultrasound signals (transmit beamforming) and for the processing of reflected ultrasound signals (receive beamforming).

The backscattered ultrasound energy depends on tissue properties such as the size, shape and density of e.g. cells/structures/components relative to the wavelength and propagation direction of sound. As a result, the frequency content of a backscattered pulse will be dependent on the characteristics of the tissue microstructure. However, the excitation and geometry of the transducer will determine the transmitted ultrasound field and therefore also heavily affect the frequency of the backscattered ultrasound. It is therefore important to introduce some kind of normalization to remove the effects of the transducer in the analysis of the frequency spectrums of the backscattered ultrasound data. This can be achieved in multiple ways. Commonly, the spectrums are divided by a spectrum received by the same transducer from a reference phantom or from a mirror plate placed in water at the same investigation depth. Used in the correct way these normalizations effectively remove the effects of the transducer from the frequency spectrum. The result is a spectrum that could give tissue specific information to the clinician.

Despite recent progress in applying ultrasound techniques in the assessment of tissue structure by spectral analysis, the technology still suffers from relatively poor signal-to-noise ratios and image resolution.

SUMMARY OF THE INVENTION

The present disclosure relates to an ultrasound system and method that introduces improvements with respect to accuracy compared to conventional ultrasound systems. A first aspect of the present disclosure relates to an ultrasound system comprising:
  a. an ultrasound transducer configured to transmit a plurality of ultrasound signals from a plurality of elements in a transducer array to a region of interest; the ultrasound transducer further configured to receive and sample a plurality of backscattered ultrasound signals from the region of interest;
  b. a processing unit configured to:
  i. calculate a local phase parameter in the time-domain for each, or for groups, of the plurality of backscattered ultrasound signals;
  ii. calculate a center frequency for each of the local phase parameters of the backscattered ultrasound signals in the time domain;
  c. a beamformer configured to perform receiver beamforming by summing the center frequencies,
  d. wherein the ultrasound system is further configured to generate at least one parameter representative of a physical property of the region of interest based on the summed center frequencies.

In frequency measurements and spectral analysis of ultrasound it is typically challenging to achieve good signal-to-noise ratios, in particular while at the same time achieving high spatial resolution. The inventor has realized that the accuracy can be improved in an ultrasound system that uses beamforming by calculating a local phase parameter in the time-domain for each, or groups, of the plurality of backscattered ultrasound signals, and by calculating a center frequency, still operating in the time-domain, before any receive beamforming is performed. In ultrasound systems there are typically a transmit beamforming part and a receive beamforming part. In the transmit beamforming the ultrasound wave transmitted by each element in the transducer array is typically individually delayed to obtain a summed beam in a focalization point. The transducer then switches to reception mode. The backscattered pressure hitting the elements are produced by scatterers in the region of interest. The pressures are converted to signals in the transducer. The signals are then delayed and averaged to create one radio frequency (RF) line in the form of an oscillating ultrasound line. This operation is commonly referred to as receive beamforming. In the presently disclosed ultrasound system the raw ultrasound signals are used directly in the receive processing. A local phase parameter is calculated in the time-domain for each of the plurality of backscattered ultrasound signals. This may be done, for example, by transforming the plurality of backscattered ultrasound signals to complex representations of the backscattered ultrasound signals, for example, by calculating a Hilbert transform. Based on the complex representations, a center frequency can then be calculated for each of the local phase parameters of the backscattered ultrasound signals in the time domain. FIG. 1B shows this additional step in the form of a processing unit (106) configured to operate on the individual backscattered ultrasound signals as described. The additional processing can be applied before or after the time delays. The receive beamforming can then be applied to the calculated center frequencies.

In further frequency analyses a model can be used to estimate sizes of structures (e.g. cells) in the region of interest. The described method has turned out to provide improved accuracy in subsequent analysis of frequencies. FIG. 3A-C show an example of a frequency image of an area. FIG. 3A shows the theoretical frequency response for structures of different size. The area 301 illustrates a well-defined area having structures of a different size, which cause a well-defined frequency shift in the image. FIG. 3B shows a frequency image for a prior art ultrasound system. FIG. 3C shows a frequency image for the presently disclosed ultrasound system.

The present disclosure further relates to an ultrasound method comprising the steps of:

a. transmitting a plurality of ultrasound signals from a plurality of elements in a transducer array to a region of interest;

b. receiving and sampling a plurality of backscattered ultrasound signals from the region of interest;

c. calculate a local phase parameter in the time-domain for each of the plurality of backscattered ultrasound signals;

d. calculating a center frequency for each of the local phase parameters of the backscattered ultrasound signals in the time domain; and e. performing receiver beamforming by summing the center frequencies; and f. generating at least one parameter representative of a physical property of the region of interest based on the summed center frequencies.

A person skilled in the art will recognize that the presently disclosed ultrasound method may be performed using any embodiment of the presently disclosed ultrasound system. Accordingly, the method may perform any step which the presently disclosed ultrasound system is configured to perform.

BRIEF DESCRIPTION OF THE DRAWINGS

Embodiments of the presently disclosed ultrasound system and method are provided in the following drawings. The drawings are exemplary and are intended to illustrate some of the features of the presently disclosed ultrasound system and method, and are not to be construed as limiting to the presently disclosed invention.

DETAILED DESCRIPTION OF THE INVENTION

The present disclosure relates to an ultrasound system comprising:

an ultrasound transducer configured to transmit a plurality of ultrasound signals from a plurality of elements in a transducer array to a region of interest, the ultrasound transducer further configured to receive and sample a plurality of backscattered ultrasound signals from the region of interest.

Figure 1A:
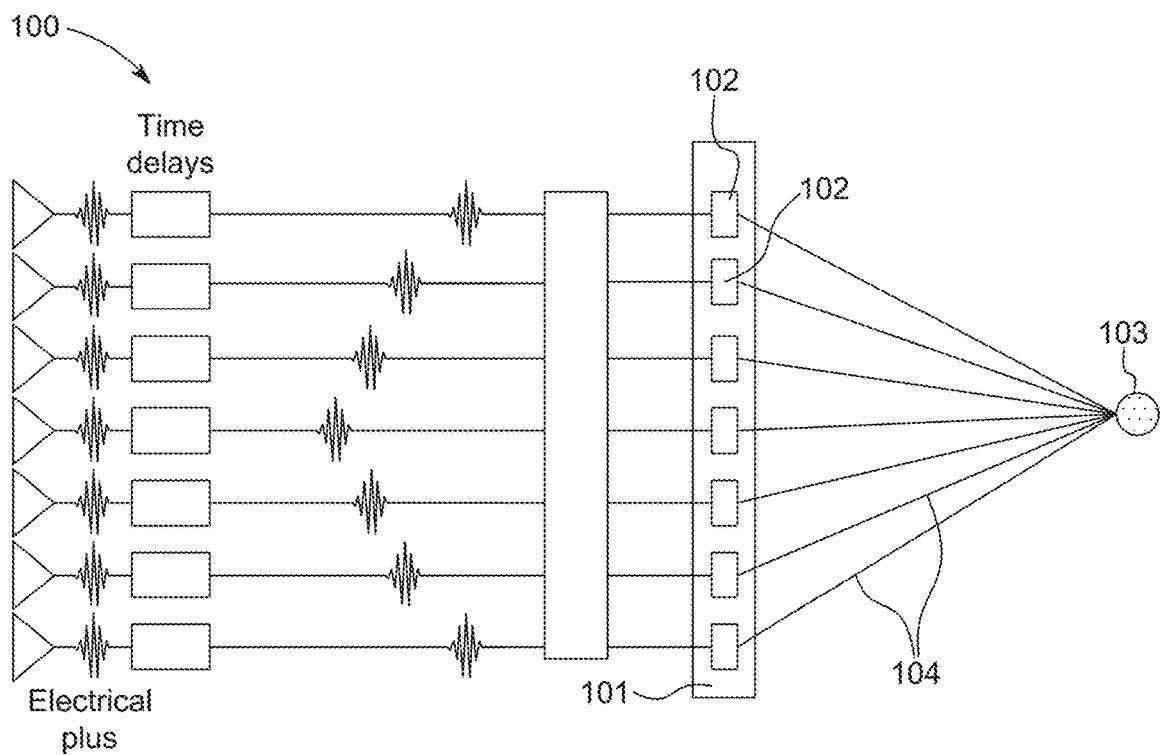
FIG. 1A shows an embodiment of a transmit side with a transmit beamformer according to one embodiment of the presently disclosed ultrasound system.
Figure 1B:
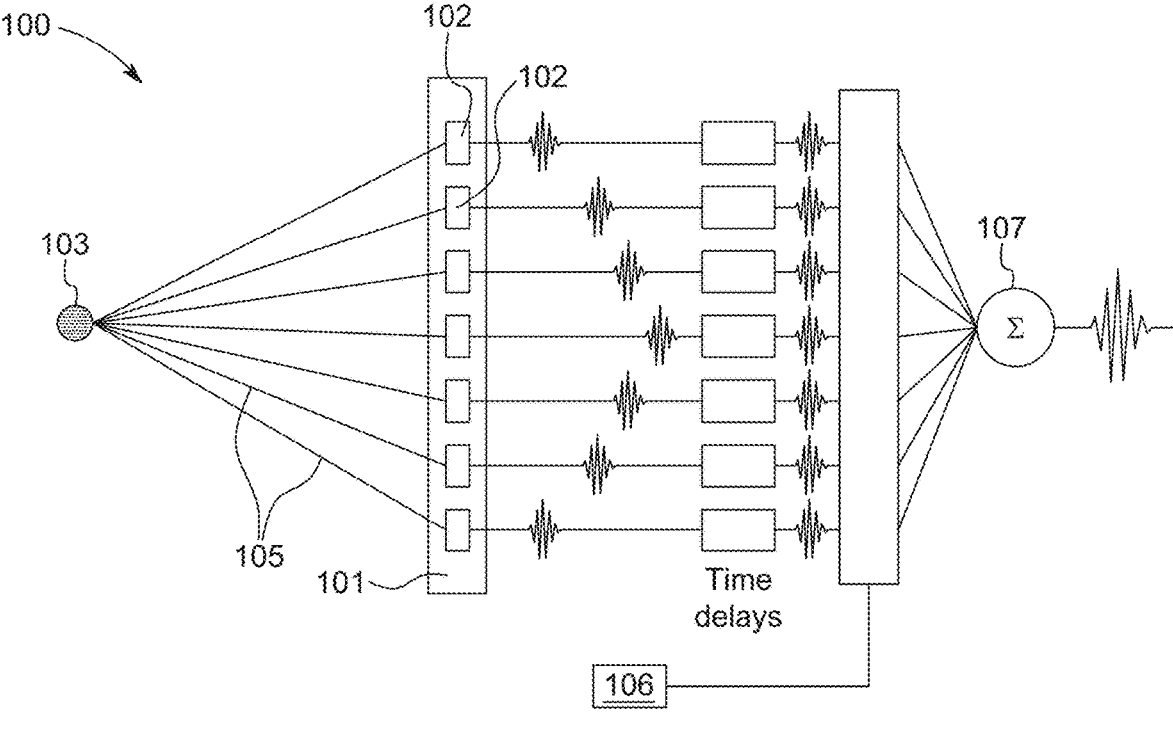
FIG. 1B shows an embodiment of a receive side with a receive beamformer according to one embodiment of the presently disclosed ultrasound system.

Preferably, the ultrasound system comprises a transmit beamformer. A person skilled in the art would, generally, know how to implement transmit beamforming. FIG. 1A shows an embodiment of a transmission side with a transmit beamformer according to one embodiment of the presently disclosed ultrasound system (100). A number of parallel pulses are generated. The pulses may typically be generated at 1-20 MHz, such as 10 MHz, but any suitable frequency is possible. The parallel pulses are individually delayed. A number of elements (102) in a transducer array (101) are configured to transmit ultrasound signals (104) to obtain a summed beam in a focalization point (103). The relative delays between the pulses may be constructed in such a way that ultrasound pulses arrive to the focalization point (103) simultaneously, with their phases aligned. Preferably, the ultrasound system further comprises a receive beamformer. A person skilled in the art would, generally, know how to implement a receive beamformer. However, the receive side of the presently disclosed ultrasound system comprises further processing. FIG. 1B shows an embodiment of a receive side with a receive beamformer according to one embodiment of the presently disclosed ultrasound system (100). The backscattered ultrasound waves (105) from one point (103) hit the elements (102) in the transducer array (101). The signals are then delayed. The delays in the receiver may correspond to time differences between the received signals in the elements (102). The ultrasound system may further comprise a processing unit (106), which may be integrated or connected to the transducer in any suitable way. The processing unit may be configured to calculate a local phase parameter in the time-domain for each of the plurality of backscattered ultrasound signals. The processing unit may be further configured to calculate a center frequency for each of the local phase parameters of the backscattered ultrasound signals in the time domain. More specifically, a local phase parameter and center frequency may be calculated for each sample in each element. If the transducer includes, for example, 64 elements and 2048 samples are received, the processing unit may be configured to calculate 2048×64 local phase parameters and center frequencies. In one embodiment, the processing unit is configured to calculate local phase parameters in the time domain for each sample in each of the plurality of backscattered ultrasound signals. The processing unit may be further configured to calculate center frequencies for all of the calculated phase parameters. The ultrasound system may further comprise a receive beamformer (107) configured to perform receiver beamforming by summing the center frequencies. A beamformer may be implemented in hardware, software, or a combination thereof. Based on the summed center frequencies and, preferably, a model of the region of interest, the processing unit may be further configured to generate at least one parameter representative of a physical property of the region of interest.

By calculating the center frequencies before the receive beamforming is performed, which can be said to break with common practice in ultrasound systems, the frequency data becomes more precise compared to doing frequency calculation after receive beamforming. Accordingly, the ultrasound system may be configured to calculate the local phase parameters and calculate the center frequencies prior to performing receiver beamforming. 'Center frequency' shall be construed broadly and cover scenarios where the center frequency is multiplied by a factor. It may be envisaged that the local phase parameters in the time-domain for each of the plurality of backscattered ultrasound signals are calculated before beamforming, whereas the center frequency for each of the local phase parameters are calculated after beamforming. Accordingly, the processing unit may be configured to: calculate a local phase parameter in the time-domain for each of the plurality of backscattered ultrasound signals.

A beamformer may be configured to perform receiver beamforming by summing the local phase parameters. The processing unit may then calculate center frequencies for the summed local phase parameters. In one embodiment, the samples that are summed in the beamforming step are weighted according to amplitudes of the backscattered ultrasound signals before center frequencies are calculated from the phase parameters.

In one embodiment, the ultrasound system is configured to calculate or compute a variance of the summed center frequencies over at least a part of the region of interest. The inventors have found that when the center frequencies are calculated before performing the receive beamforming, the variance of the summed center frequencies can be used to characterize tissue in the region of interest.

Preferably, the processing is configured to calculate a center frequency for each of the local phase parameters of the backscattered ultrasound signals in the time domain. The processing unit may thereby be configured to calculate the center frequencies based on the backscattered ultrasound signals without frequency transformations. The beamformer can then sum the center frequency, preferably only the center frequencies. The system and method may be based on an assumption that the backscattered pulses are Gaussian shaped.

According to one embodiment, the ultrasound system is an ultrasound system for characterizing tissue, wherein the ultrasound transducer is configured to transmit a plurality of ultrasound signals from a plurality of elements in a transducer array to a region of interest in the tissue, and wherein the system is further configured to characterize the tissue based on the summed center frequencies. The backscattered ultrasound energy will depend on tissue properties such as the size, shape and density of e.g. cells/structures relative to the wavelength and propagation direction of sound. As a result, the frequency content of a backscattered pulse will be dependent on the characteristics of the tissue microstructure. The ultrasound system may therefore be further configured to estimate structure sizes using backscattered center frequencies.

According to a further embodiment, the ultrasound system is an ultrasound system for characterizing arterial wall and atherosclerotic plaque, wherein the ultrasound transducer is configured to transmit a plurality of ultrasound signals from a plurality of elements in a transducer array to a region of interest in at least one artery wall, and wherein the ultrasound system is further configured to characterize the arterial atherosclerotic plaque in the at least one artery wall based on the summed center frequencies. Other applications are possible, including, but not limited to, characterization of myocardium, breast lesion characterization, thyroid lesions, prostate lesions, detection of micro metastases in excised lymph nodes, and quantifying liver steatosis and detection of cervical ripening.

Figure 5:
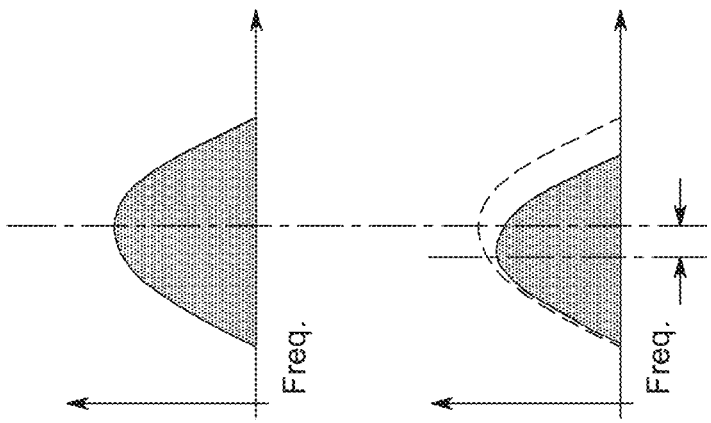
FIG. 5 shows an illustration of center frequency shifts for different scatterer sizes.
Figure 5:
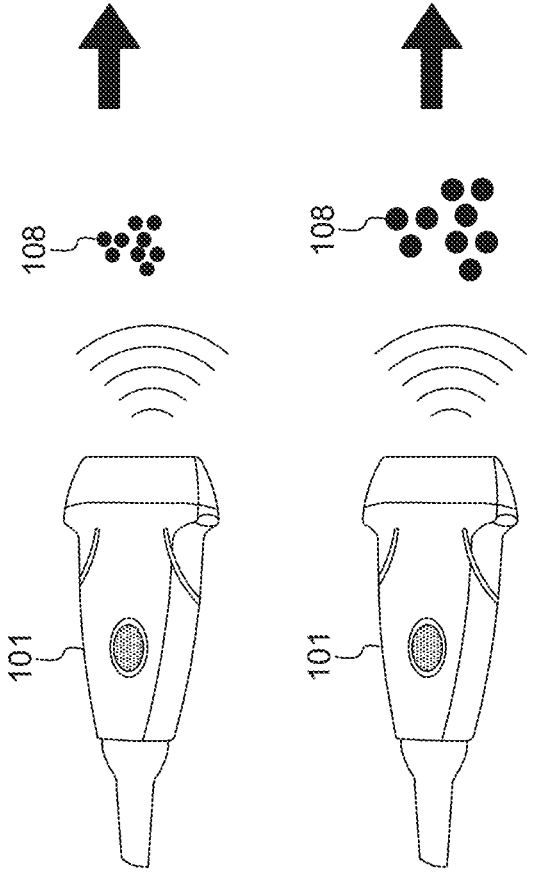

The ultrasound system is configured to generate at least one parameter representative of a physical property of the region of interest based on the summed center frequencies and a model of the region of interest. The model of the region of interest may be a physical model comprising information about the backscattering for different structures in the region of interest. A person skilled in the art would be able to implement such a model, which may be a physical model of the structure, comprising a mathematical description of how a material and/or sizes of structures scatter ultrasound waves, in particular how the backscattered center frequency correlates with scatterer radius. FIG. 5 shows an example of center frequency shifts for different sizes of structures (108). A transducer (101) is configured to transmit ultrasound signals and receive backscattered ultrasound signals.

Figure 4A:
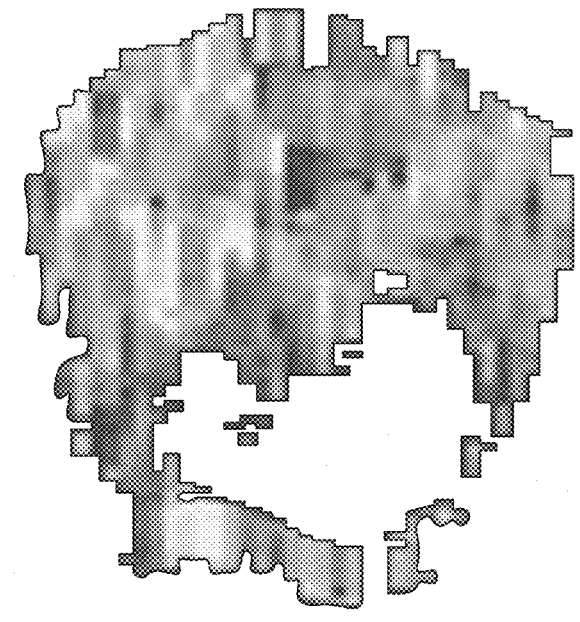
FIG. 4 shows a comparison of ultrasound images of carotid plaque using a conventional ultrasound systems (A) and using the presently disclosed ultrasound system (B)
Figure 4B:
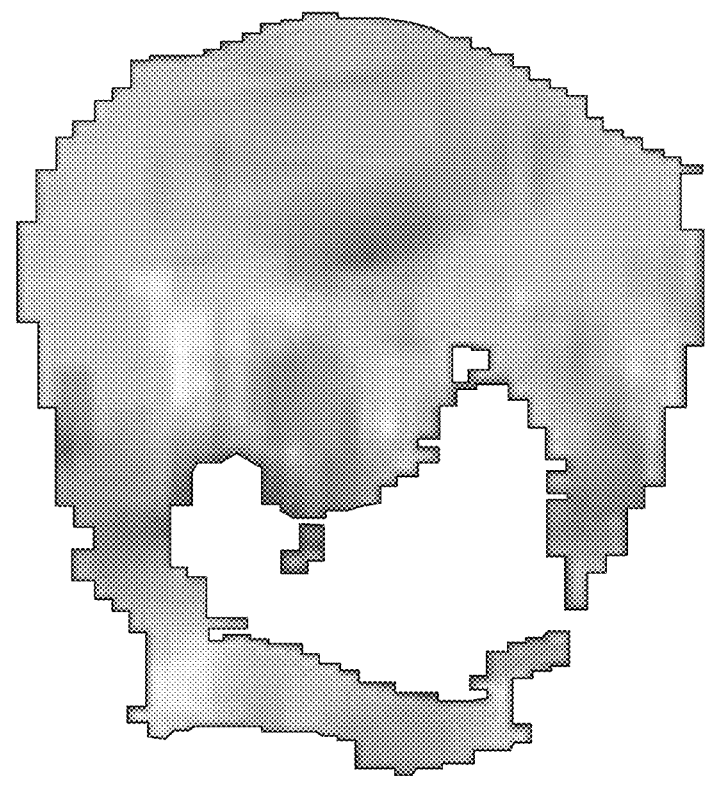

The ultrasound system may be an ultrasound imaging device. A useful way of presenting the center frequencies, or center frequency shifts, or other parameters generated from the center frequencies, may be by means of an image, such as frequency image, wherein colors or a greyscale represent different frequencies. In such an embodiment the ultrasound system may further comprise a display for displaying at least one image of the region of interest. The at least one image may comprise a representation of sizes of structures in the region of interest reflecting the plurality of ultrasound signals. The processing unit may be further configured to compute and/or extract the sizes of structures based on the summed center frequencies. It may not be necessary to present an image to the user. Alternatively, the system may be configured to generate frequencies in the form of, for example, a list, table or database, from which further parameters can be derived. Moreover, the image may comprise a representation, wherein arterial plaque has been characterized and wherein the image comprises a translated representation of a structure or composition of atherosclerotic plaque and/or of a risk associated with the arterial plaque, for example, expressed as a color map. FIG. 4 shows a comparison of ultrasound images of plaque using a conventional ultrasound system, wherein frequency analysis/processing is performed after beamforming (A) and using the presently disclosed ultrasound system (B). As can be seen, the presently disclosed ultrasound system provides a greater accuracy, which may be perceived as improved spatial resolution. The processing unit may be configured to estimate sizes of cells or components, such as fibers and/or non-cellular substances, in the region of interest based on the summed center frequencies.

In one embodiment, the ultrasound system is configured to determine a tissue composition, preferably a carotid plaque composition based on the summed center frequencies. The tissue composition or the carotid plaque composition may comprise a quantified value of a physical property of an artery wall, such as a percentage or a fraction of the artery wall, sizes of cells and/or structures, or a quantified diagnostic value, such as a calculated plaque risk score. The ultrasound system may be configured to detect plaque components that are associated with the risk of plaque rupture. It has been found that a correlation exists between a center frequency shift and the amount of collagen and smooth muscle cells (positively) and macrophages and core size (negatively). These plaque characteristics coincide with the description of stable plaque and vice versa.

The plurality of elements arranged in an array in the transducer are typically configured to generate one line of an image. The ultrasound system may therefore be configured to generate a line of an image based on the summed center frequencies and a model of the region of interest. If the process is repeated, i.e. a plurality of ultrasound signals are transmitted, local phase parameter and center frequencies are calculated, and receiver beamforming is performed, a whole image comprising a plurality of lines may be generated. The transducer probe in the example of FIG. 1A comprises 7 elements (102) configured to transmit ultrasound signals. Typical transducers have, for example, 64, 192, 256 or 512 elements arranged in one row. The transducer may also have elements arranged in an array of m×n elements, i.e. m elements in one direction and n elements in another direction. The elements may be piezoelectric elements configured to convert electrical signals to ultrasound signals and to transform the backscattered ultrasound signals to received electrical signals that are further processed by the processing unit. FIG. 1B shows the receive side wherein 7 elements (102) are configured to covert ultrasound waves to electrical signals. Moreover, the ultrasound system may be configured to repeat a process of transmitting the plurality of ultrasound signals, receiving the plurality of backscattered ultrasound signals and processing the received plurality of backscattered ultrasound signals for a number of focal lengths.

The local phase parameter may typically be calculated by transforming the plurality of backscattered ultrasound signals to complex representations of the backscattered ultrasound signals, for example, by calculating a Hilbert transform or quadrature demodulation. The complex data can be used to obtain time domain phase differences between samples in the backscattered data and used for center frequency estimation. One approach is to measure the phase derivative, usually referred to as the instantaneous frequency. Another commonly used method to derive a phase difference is the complex autocorrelation method.

Example of Center Frequency Calculations

The center frequency can be calculated according the following example. A number of samples are collected in each element in the transducer array. Example, wherein Sample is a vector from n=1 to m:

sample HT=Hilbert Transform of Sample;

$$sampleComplex(n) = Sample \ (n) + i * sampleHT(n);$$

sampleConj(n)=sampleComplex(n)*conj(sampleComplex(n−1)), where conj is the conjugate [each sample in sampleConj may be averaged with some nearby samples];

Phase difference between samples=PD=arctan(IMAG (sampleConj) REAL(sampleConj)), where arctan is a four-quadrant inverse tangent and IMAG is the imaginary part and REAL is the real part;

Center frequency=PD(2*pi)*Fs, where Fs is the sampling frequency of Sample

Ultrasound Method

Figure 2:
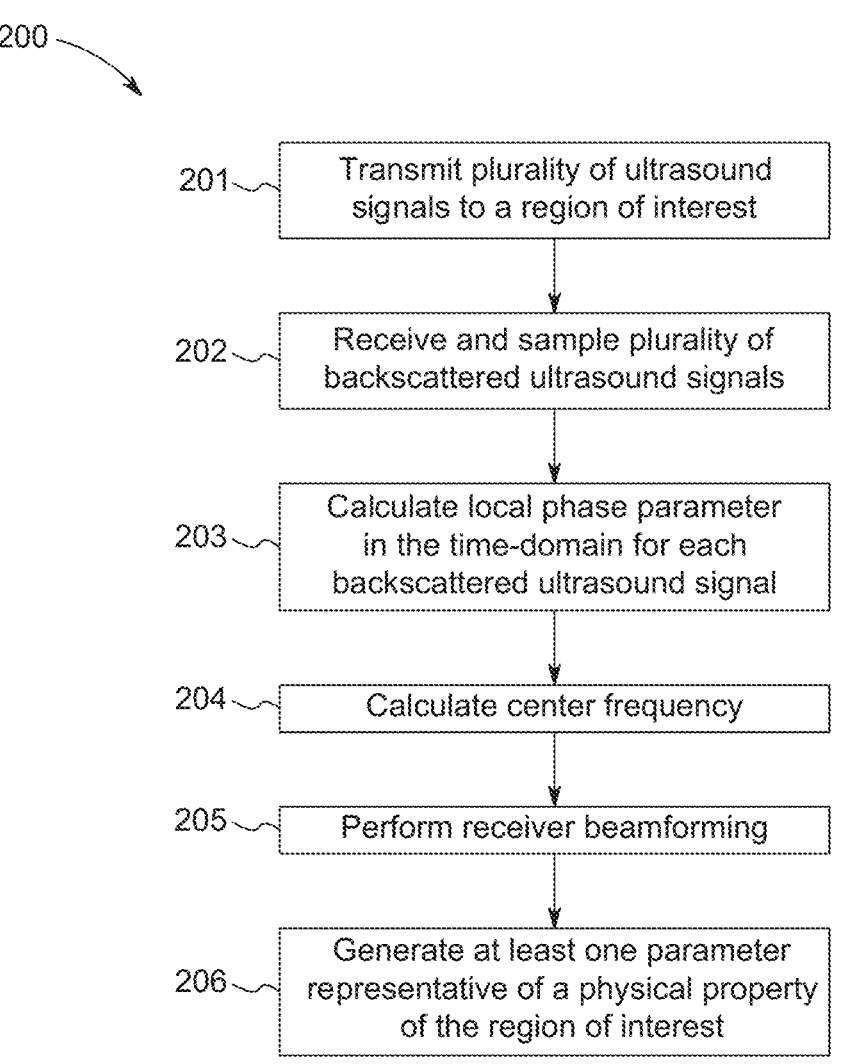
FIG. 2 shows an embodiment of the presently disclosed ultrasound method.
Figure 3A:
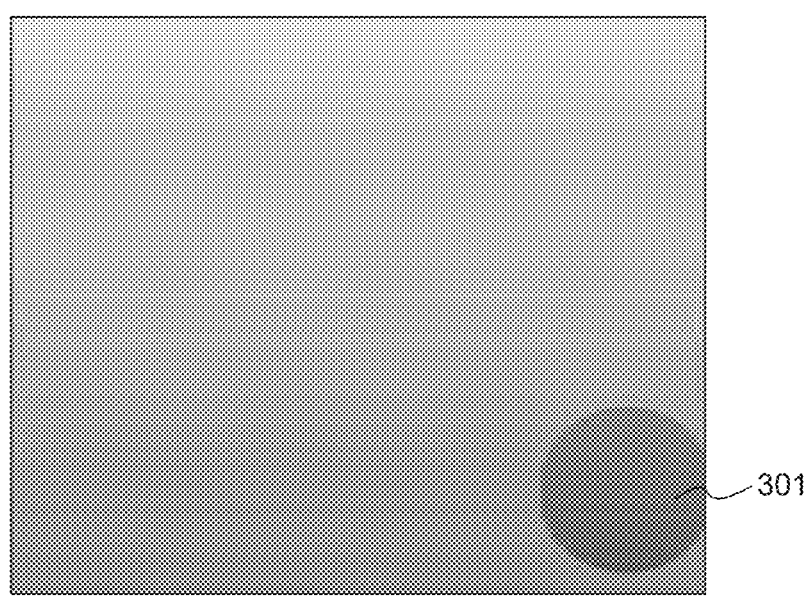
FIG. 3 shows a comparison of theoretical backscattered frequencies for variations in structures (A), measured backscattered frequencies using conventional ultrasound systems (B) and measured backscattered frequencies using the presently disclosed ultrasound system (C)
Figure 3B:
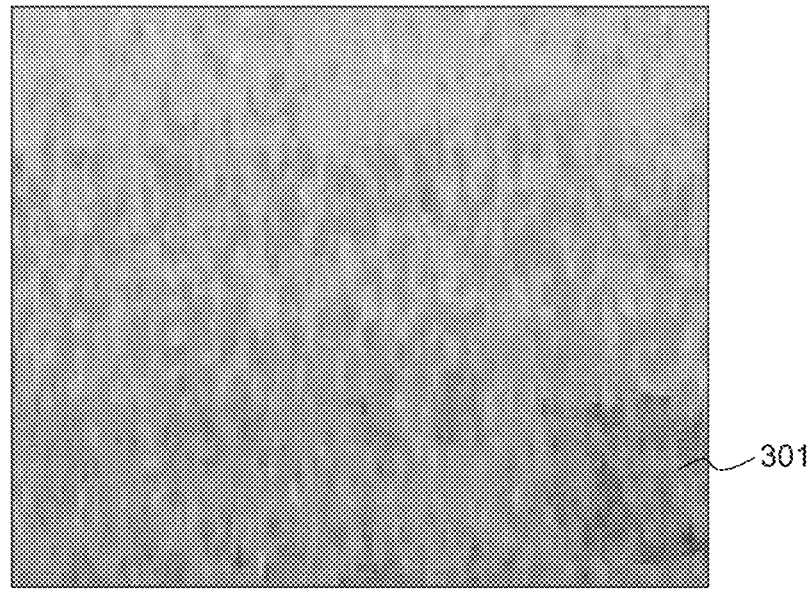
Figure 3C:

The present disclosure further relates to an ultrasound method for generating at least one parameter representative of a physical property of the region of interest. FIG. 2 shows an embodiment of the presently disclosed ultrasound method (200). In the embodiment the ultrasound method (200) comprises the steps of:

a. transmitting (201) a plurality of ultrasound signals from a plurality of elements in a transducer array to a region of interest;

b. receiving and sampling (202) a plurality of backscattered ultrasound signals from the region of interest;

c. calculating (203) a local phase parameter in the time-domain for each of the plurality of backscattered ultrasound signals;

d. calculating (204) a center frequency for each of the local phase parameters of the backscattered ultrasound signals in the time domain;

e. performing (205) receiver beamforming by summing the center frequencies; and f. generating (206) at least one parameter representative of a physical property of the region of interest based on the summed center frequencies.

Preferably, the step of calculating the center frequencies is performed prior to the step of performing receiver beamforming. The steps of the method may be performed in a sequence. Preferably, the method comprises the step of performing transmit beamforming.

Further Details of the Invention

1. An ultrasound system comprising:
an ultrasound transducer configured to transmit a plurality of ultrasound signals from a plurality of elements in a transducer array to a region of interest; the ultrasound transducer further configured to receive and sample a plurality of backscattered ultrasound signals from the region of interest;
a processing unit configured to:
calculate a local phase parameter in the time-domain for each, or groups, of the plurality of backscattered ultrasound signals;
calculate a center frequency for each of the local phase parameters of the backscattered ultrasound signals in the time domain;
a beamformer configured to perform receiver beamforming by summing the center frequencies,
wherein the ultrasound system is further configured to generate at least one parameter representative of a physical property of the region of interest based on the summed center frequencies.

2. The ultrasound system according to item 1, wherein the ultrasound system is an ultrasound system for characterizing tissue, wherein the ultrasound transducer is configured to transmit a plurality of ultrasound signals from a plurality of elements in a transducer array to a region of interest in the tissue, and wherein the system is further configured to characterize the tissue based on the summed center frequencies.

3. The ultrasound system according to any one of the preceding items, wherein the ultrasound system is an ultrasound system for characterizing atherosclerotic plaque, wherein the ultrasound transducer is configured to transmit a plurality of ultrasound signals from a plurality of elements in a transducer array to a region of interest in at least one artery wall, and wherein the ultrasound system is further configured to characterize the atherosclerotic plaque in the at least one artery wall based on the summed center frequencies.

4. The ultrasound system according to any one of the preceding items, wherein the ultrasound system is configured to generate at least one parameter representative of a physical property of the region of interest based on the summed center frequencies and a model of the region of interest.

5. The ultrasound system according to item 4, wherein the model of the region of interest is a physical model comprising information about the backscattering for different structures in the region of interest.

6. The ultrasound system according to any one of the preceding items, wherein the ultrasound system is further configured to generate a line of an image based on the summed center frequencies.

7. The ultrasound system according to item 6, wherein the ultrasound system is configured to repeat the transmission of a plurality of ultrasound signals, the calculation of a local phase parameter and center frequencies, and performing receiver beamforming to generate an image comprising a plurality of lines.

8. The ultrasound system according to any one of the preceding items, wherein the ultrasound system is configured to calculate the local phase parameters and calculate the center frequencies prior to performing receiver beamforming.

9. The ultrasound system according to any one of the preceding items, wherein the ultrasound system is further configured to determine a plaque composition, such as a carotid plaque composition, based on the summed center frequencies.

10. The ultrasound system according to item 9, wherein the carotid plaque composition comprises a quantified value of a physical property of an artery wall, such as a percentage or a fraction of the artery wall, sizes of cells and/or structures, or a quantified diagnostic value, such as a calculated plaque risk score.

11. The ultrasound system according to any one of the preceding items, wherein the ultrasound transducer comprises piezoelectric elements configured to convert electrical signals to ultrasound signals and to transform the backscattered ultrasound signals to received electrical signals that are further processed by the processing unit.

12. The ultrasound system according to any one of the preceding items, further comprising a display for displaying the at least one image of the region of interest.

13. The ultrasound system according to any one of the preceding items, wherein the at least one image comprises a representation of sizes of structures in the region of interest reflecting the plurality of ultrasound signals.

14. The ultrasound system according to item 13, wherein the processing unit is further configured to compute and/or extract the sizes of structures based on the summed center frequencies.

15. The ultrasound system according to any one of the preceding items, wherein the processing unit is configured to estimate sizes of cells or components, such as fibers and/or non-cellular substances, in the region of interest based on the summed center frequencies.

16. The ultrasound system according to any one of the preceding items, wherein the processing unit is configured to calculate the center frequencies based on the backscattered ultrasound signals without frequency transformations.

17. The ultrasound system according to any one of the preceding items, wherein the beamformer is configured to sum only the center frequencies.

18. The ultrasound system according to any one of the preceding items, wherein the ultrasound system is configured to repeat a process of transmitting the plurality of ultrasound signals, receiving the plurality of backscattered ultrasound signals and processing the received plurality of backscattered ultrasound signals for a number of focal lengths.

19. The ultrasound system according to any one of the preceding items, wherein the local phase parameter is calculated by transforming the plurality of backscattered ultrasound signals to complex representations of the backscattered ultrasound signals, preferably by calculating a Hilbert transform.

20. The ultrasound system according to item 19, wherein the center frequencies are calculated based on the complex representations.

21. An ultrasound method comprising the steps of:
transmitting a plurality of ultrasound signals from a plurality of elements in a transducer array to a region of interest;
receiving and sampling a plurality of backscattered ultrasound signals from the region of interest;
calculating a local phase parameter in the time-domain for each of the plurality of backscattered ultrasound signals;
calculating a center frequency for each of the local phase parameters of the backscattered ultrasound signals in the time domain; and
performing receiver beamforming by summing the center frequencies; and
generating at least one parameter representative of a physical property of the region of interest based on the summed center frequencies.

22. The ultrasound method according to item 21, wherein the steps are sequential.

23. The ultrasound method according to any one of items 21-22, wherein the step of calculating the center frequencies is performed prior to the step of performing receiver beamforming.

24. An ultrasound system comprising:
an ultrasound transducer configured to transmit a plurality of ultrasound signals from a plurality of elements in a transducer array to a region of interest; the ultrasound transducer further configured to receive and sample a plurality of backscattered ultrasound signals from the region of interest;
a processing unit configured to:
calculate a local phase parameter in the time-domain for each of the plurality of backscattered ultrasound signals;
a beamformer configured to perform receiver beamforming by summing the local phase parameters,
the processing unit further configured to:
calculate a center frequency for each of the local phase parameters of the backscattered ultrasound signals in the time domain; and
wherein the ultrasound system is further configured to generate at least one parameter representative of a physical property of the region of interest based on the summed center frequencies.

The invention claimed is:

1. An ultrasound system comprising:
an ultrasound transducer configured to transmit a plurality of ultrasound signals from a plurality of elements in a transducer array to a region of interest; the ultrasound transducer further configured to receive and sample a plurality of backscattered ultrasound signals from the region of interest;
a processing unit configured to:

calculate a local phase parameter in the time-domain for each of the plurality of backscattered ultrasound signals, the local phase parameter comprising a time domain difference;

calculate a center frequency for each of the local phase parameters of the backscattered ultrasound signals in the time domain; and a beamformer configured to perform receiver beamforming by summing the center frequencies, wherein the processing unit is further configured to generate at least one parameter representative of a physical property representative of sizes of cells or components, or a plaque composition, of the region of interest based on the summed center frequencies.

2. The ultrasound system according to claim 1, wherein the processing unit is configured to calculate or compute a variance of the summed center frequencies over at least a part of the region of interest.

3. The ultrasound system according to claim 1, wherein the processing unit is configured to generate the at least one parameter based on the summed center frequencies and a model of the region of interest, wherein the model of the region of interest is a physical model of structures of the region of interest comprising a mathematical description of how a material and/or sizes of the structures in the region of interest scatter ultrasound waves, wherein the model comprises a mathematical description of how the center frequencies correlate with scatterer radius.

4. The ultrasound system according to claim 1, wherein the at least one image comprises a representation of sizes of structures in the region of interest reflecting the plurality of ultrasound signals.

5. The ultrasound system according to claim 4, wherein the processing unit is further configured to compute and/or extract the sizes of structures based on the summed center frequencies.

6. The ultrasound system according to claim 1, wherein the processing unit is configured to calculate the center frequencies based on the backscattered ultrasound signals without frequency transformations.

7. The ultrasound system according to claim 1, wherein the beamformer is configured to sum only the center frequencies.

8. The ultrasound system according to claim 1, wherein the processing unit is configured to repeat a process of transmitting the plurality of ultrasound signals, receiving the plurality of backscattered ultrasound signals and processing the received plurality of backscattered ultrasound signals for a number of focal lengths.

9. The ultrasound system according to claim 1, wherein the local phase parameter is calculated by transforming the plurality of backscattered ultrasound signals to complex representations of the backscattered ultrasound signals.

10. A computer-implemented ultrasound method comprising the steps of:

transmitting a plurality of ultrasound signals from a plurality of elements in a transducer array to a region of interest;

receiving and sampling a plurality of backscattered ultrasound signals from the region of interest;

calculating a local phase parameter in the time-domain for each of the plurality of backscattered ultrasound signals, the local phase parameter comprising a time domain difference;

calculating a center frequency for each of the local phase parameters of the backscattered ultrasound signals in the time domain; and performing receiver beamforming by summing the center frequencies; and generating at least one parameter representative of a physical property representative of sizes of cells or components, or a plaque composition, of the region of interested based on the summed center frequencies.

11. An ultrasound system comprising:

an ultrasound transducer configured to transmit a plurality of ultrasound signals from a plurality of elements in a transducer array to a region of interest; the ultrasound transducer further configured to receive and sample a plurality of backscattered ultrasound signals from the region of interest;

a processing unit configured to:

calculate a local phase parameter in the time-domain for each of the plurality of backscattered ultrasound signals, the local phase parameter comprising a time domain difference;

a beamformer configured to perform receiver beamforming by summing the local phase parameters, the processing unit further configured to:

calculate a center frequency for each of the local phase parameters of the backscattered ultrasound signals in the time domain; and wherein the processing unit is further configured to generate at least one parameter representative of a physical property representative of sizes of cells or components, or a plaque composition, of the region of interest based on the summed center frequencies.

* * * * *